(12) United States Patent
Pickert et al.

(10) Patent No.: US 10,595,799 B2
(45) Date of Patent: Mar. 24, 2020

(54) X-RAY ASSEMBLY INCLUDING A PLURALITY OF X-RAY FACILITIES

(71) Applicant: Siemens Healthcare GmbH, Erlangen (DE)

(72) Inventors: Nils Pickert, Erlangen (DE); Christian Dressler, Herzogenaurach (DE); Maik Bittner, Langensendelbach (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/521,862

(22) Filed: Jul. 25, 2019

(65) Prior Publication Data

US 2020/0029921 A1  Jan. 30, 2020

(30) Foreign Application Priority Data

Jul. 26, 2018 (EP) .................................. 18185766

(51) Int. Cl.
*A61B 6/00* (2006.01)
*A61B 6/03* (2006.01)

(52) U.S. Cl.
CPC .............. *A61B 6/4405* (2013.01); *A61B 6/40* (2013.01); *A61B 6/584* (2013.01); *A61B 6/032* (2013.01); *A61B 6/4441* (2013.01); *A61B 6/4464* (2013.01); *A61B 6/548* (2013.01)

(58) Field of Classification Search
CPC ......... A61B 6/032; A61B 6/40; A61B 6/4405; A61B 6/4441; A61B 6/4464; A61B 6/548; A61B 6/584
See application file for complete search history.

(56) References Cited

U.S. PATENT DOCUMENTS

| | | |
|---|---|---|
| 2002/0150214 A1 | 10/2002 | Spahn |
| 2005/0011706 A1 | 1/2005 | Johnson |
| 2005/0169424 A1 | 8/2005 | Bruder |
| 2007/0143147 A1 | 6/2007 | Petrick |
| 2014/0105359 A1 | 4/2014 | Foos |

(Continued)

FOREIGN PATENT DOCUMENTS

| | | |
|---|---|---|
| DE | 10215987 A1 | 11/2003 |
| DE | 102013219193 A1 | 3/2015 |

(Continued)

OTHER PUBLICATIONS

European Search Report for European Patent Application No. 18185766.5-1124 dated Feb. 11, 2019, with English Translation.

(Continued)

*Primary Examiner* — Mark R Gaworecki
(74) *Attorney, Agent, or Firm* — Lempia Summerfield Katz LLC

(57) ABSTRACT

System and methods are provided for an X-ray assembly including at least two X-ray facilities each with a control facility and a recording assembly including an X-ray tube and an X-ray detector. At least one of the X-ray facilities is a mobile X-ray facility with a mobile carrier carrying the recording assembly. The control facility of least one of the at least one mobile X-ray facility is configured to control the image recording operation of the respective X-ray facility using control data received from another control facility via a communication connection and/or to transfer at least one recorded image dataset to at least one further control facility via the communication connection.

18 Claims, 5 Drawing Sheets

(56) References Cited

U.S. PATENT DOCUMENTS

| | | |
|---|---|---|
| 2015/0327833 A1 | 11/2015 | Tsuchiya |
| 2016/0213346 A1 | 7/2016 | Benndorf |
| 2016/0295094 A1 | 10/2016 | Endoh |
| 2016/0345920 A1 | 12/2016 | Tajima |
| 2016/0374640 A1 | 12/2016 | Tamura |
| 2018/0021008 A1 | 1/2018 | Hong |

FOREIGN PATENT DOCUMENTS

| | | |
|---|---|---|
| EP | 3267428 A1 | 1/2018 |
| JP | 2000287962 A | 10/2000 |
| JP | 2002125960 A | 5/2002 |
| JP | 2004337264 A | 12/2004 |
| JP | 2005199046 A | 7/2005 |
| JP | 2005205220 A | 8/2005 |
| JP | 2007044136 A | 2/2007 |
| JP | 2007152112 A | 6/2007 |
| JP | 2011030660 A | 2/2011 |
| JP | 2015196073 A | 11/2015 |
| JP | 2016190008 A | 11/2016 |
| JP | 2016214706 A | 12/2016 |
| JP | 2016220896 A | 12/2016 |
| JP | 2017051420 A | 3/2017 |
| KR | 20160119307 A | 10/2016 |

OTHER PUBLICATIONS

Pickert, Nils, "Zeitsynchronisierte Biplan-Aufnahmen", Sep. 17, 2012 with English Translation. pp. 1-2.
Japanese Office Action for Japanese Patent Application No. 2019-108058, dated Jan. 7, 2020, with English translation.

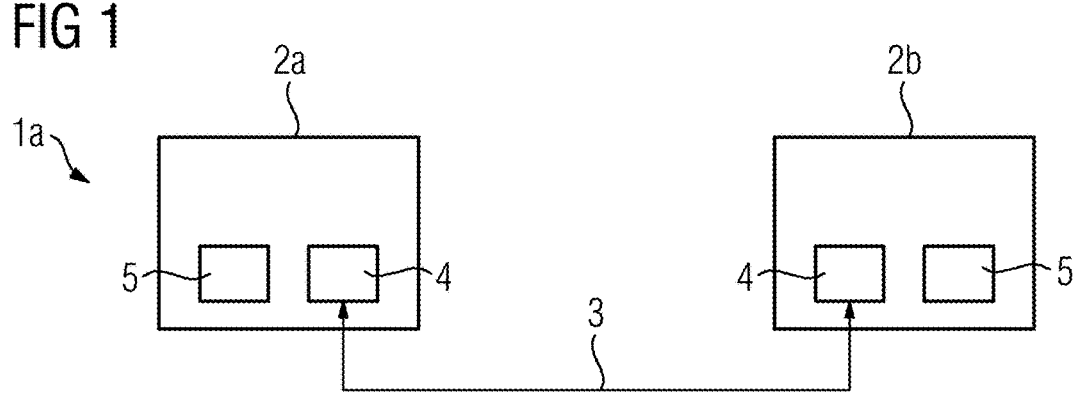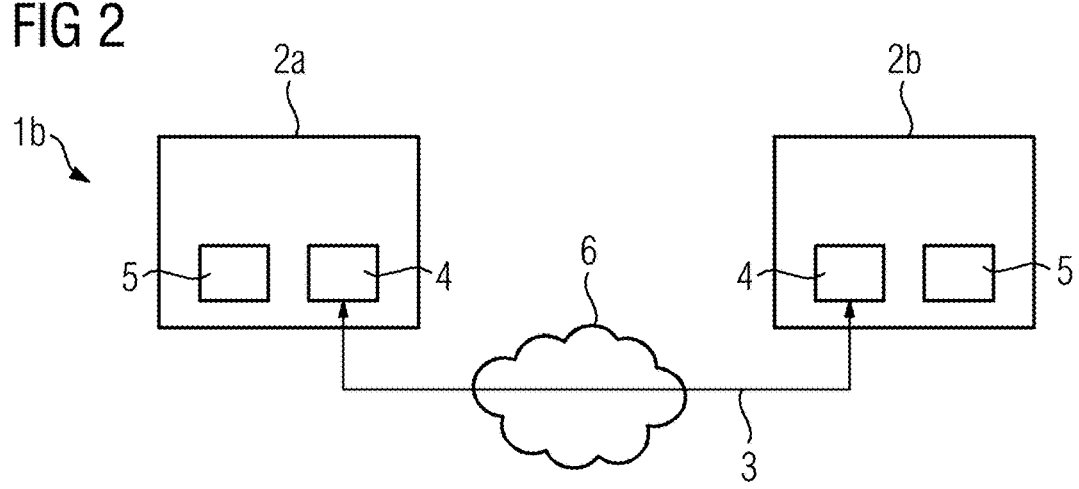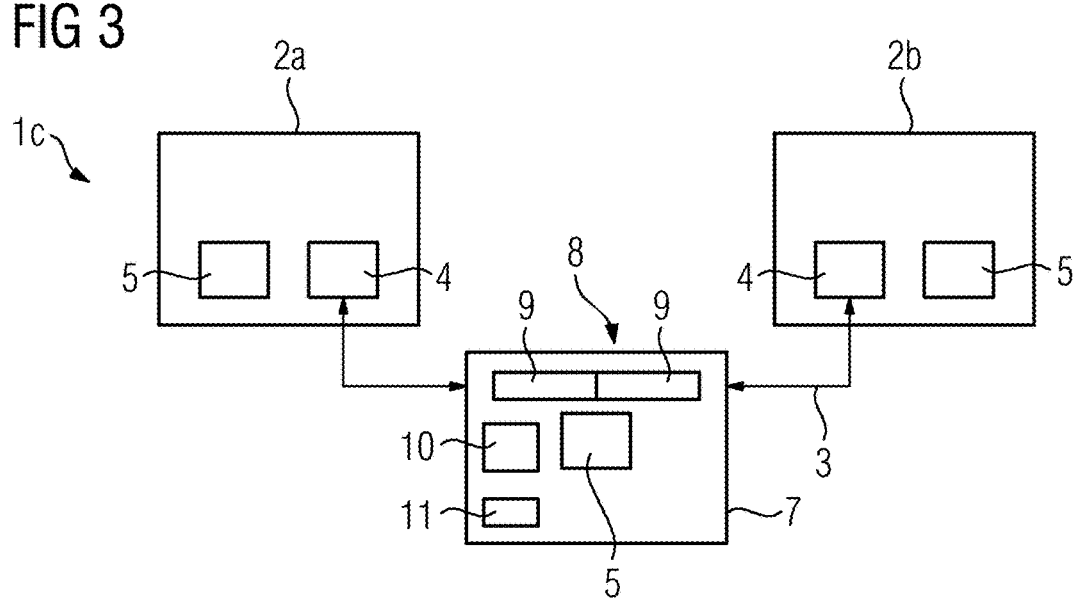

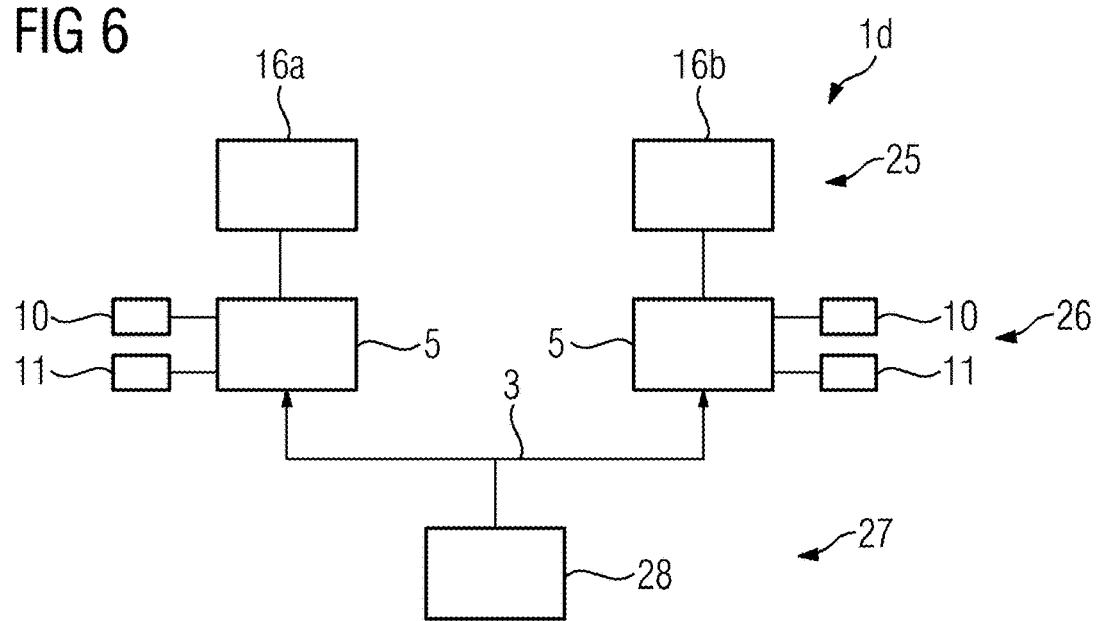
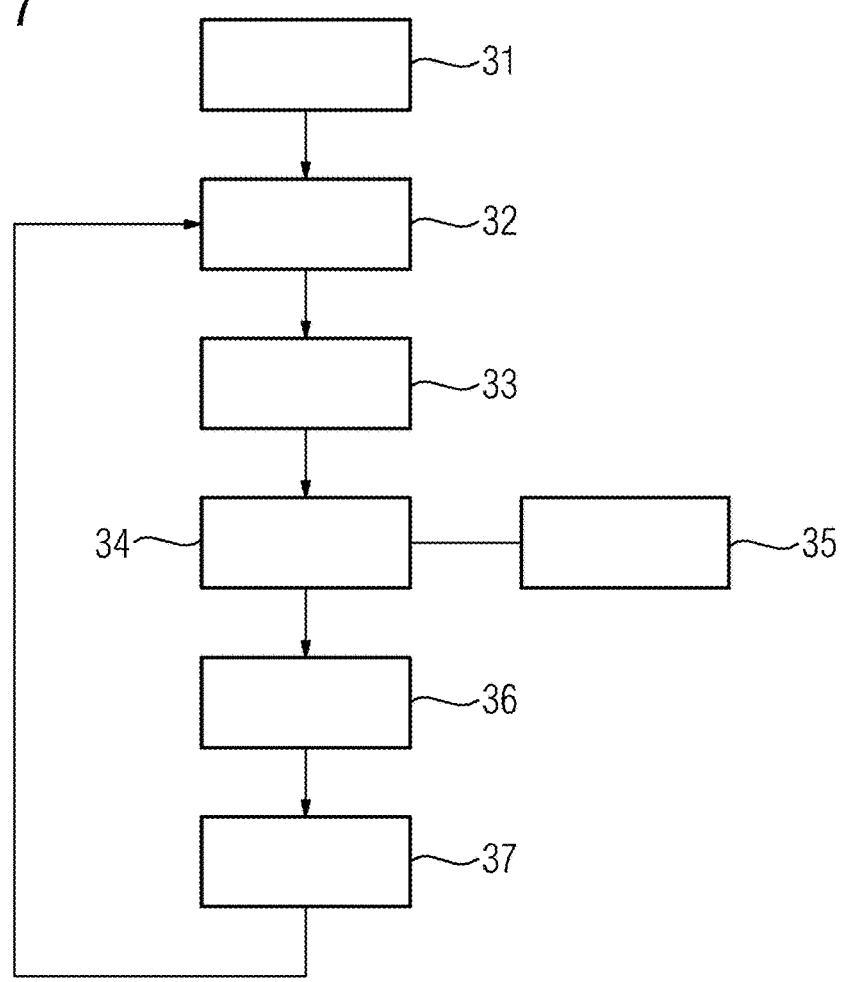

X-RAY ASSEMBLY INCLUDING A PLURALITY OF X-RAY FACILITIES

CROSS REFERENCE TO RELATED APPLICATIONS

This application claims the benefit of EP18185766.5, filed on Jul. 26, 2018, which is hereby incorporated by reference in its entirety.

FIELD

Embodiments relate to an X-ray assembly including at least two X-ray facilities each with a control facility and a recording assembly including an X-ray tube and an X-ray detector, where at least one of the X-ray facilities is a mobile X-ray facility with a mobile carrier carrying the recording assembly.

BACKGROUND

In addition to permanently installed X-ray facilities, mobile X-ray facilities, for example so-called mobile C-arms are known, that include a carrier provided with a mobility facility, for example wheels, and thus may be moved and positioned freely in the room. In terms of performance, in the case of both 2D imaging and 3D imaging, such mobile X-ray facilities are increasingly similar to permanently installed X-ray facilities and when the mobility facility is also assigned a propulsion facility, may be configured as self-propelled, thus providing a patient table or the like to be approached with a high degree of accuracy or also highly reliable repositioning. An advantage of such mobile X-ray facilities is increased flexibility since the mobile X-ray facility may be removed from the room if required and/or moved into a less disruptive position that may be useful when examinations and/or interventions are to be performed on the patient.

In the case of permanently installed X-ray facilities, for example angiographic systems with one or two permanently installed C-arms, the use of the room is defined for specific applications. For example, in the case of a permanently installed biplane X-ray facility operated with only one of the two recording assemblies (single plane operation) and when the recording assembly that is not required and the C-arm are put into a parked position, it is not possible for the permanently installed X-ray facilities to be completely removed from the clinical area and hence the work of the staff in the examination or treatment room may be impeded. A combination of a permanently installed biplane angiography X-ray facility with a sliding-gantry CT facility is also known where a patient table is configured to be rotatable by 90° to switch between modalities. This is necessary since the C-arm of the biplane angiography X-ray facility, that is permanently mounted on the floor, cannot be moved out of the patient axis and thus it is necessary for the sliding-gantry CT X-ray facility to be positioned rotated by 90° relative to the biplane angiography X-ray facility. A sliding-gantry CT X-ray facility includes where the gantry maybe guided along rails, for example between two adjacent rooms.

Therefore, biplane X-ray facilities require more space that also results in an awkward workflow in the case of a combined biplane angiography/CT apparatus.

In addition to diagnostic angiography, simultaneous imaging in different recording geometries ("multiplane imaging") may also be useful in many fields of application, for example, with image-guided minimally invasive interventions on a patient. For example, the progress of pedicle screws in the spine, the progress of needles in the lungs/liver, the advancement of catheters in the heart/brain may be monitored from different viewing angles, for example, different projection angles, in order to avoid incorrect positioning and/or even injuries to sensitive parts of the anatomy.

Permanently installed biplane angiography X-ray facilities, that may, for example, include two C-arms each with assigned recording assemblies, are already known and are widely used. However, it has been found that, especially in situations in which costs should or must be saved, due to the mobile X-ray facilities, workaround solutions are sought with which two independent mobile X-ray facilities with C-arms are used and operated manually as a biplane system. However, this is extremely problematic if, for example, the C-arms with the recording assemblies provided thereon are to be rotated with the same angular velocity and in the same direction. Two people may be used to move the C-arms at the same speed in response to spoken commands. Human interaction entails iterative correction steps and does not guarantee a perfectly perpendicular view or a fixed angular difference of 45°. However, multiple correction steps entail a higher radiation dose, increased use of contrast agents, a longer recording time and additional staffing requirements.

However, it is also possible to use only one single C-arm with a recording assembly. The C-arm has to be moved together with the recording assembly between at least two different positions and angles. This option is extremely complex, takes a lot of time and is also dangerous since the movement has to take place around the patient, who is covered with a sterile cover and connected to other appliances, for example respirators, microscopes, endoscopes, navigation systems and the like. The need for very frequent changes between anterior-posterior positioning and lateral positioning entails immense effort.

A further problem is encountered when fixed and/or mobile X-ray facilities include an additional "monitor trolley" on which, for example, a depiction facility and an operating facility for the respective X-ray facility may be provided. The use of a plurality of X-ray facilities also requires a plurality of such monitor trolleys even though the space available inside examination and/or treatment rooms is frequently already tight.

BRIEF SUMMARY AND DESCRIPTION

The scope of the present invention is defined solely by the appended claims and is not affected to any degree by the statements within the summary. The present embodiments may obviate one or more of the drawbacks or limitations in the related art Embodiments provide a system and method for simplifying the use of mobile X-ray facilities in an X-ray assembly with at least two X-ray facilities.

Embodiments provide an X-ray assembly where the X-ray facilities each include a communication interface for establishing a communication connection between the control facilities of the X-ray facilities and/or between an intermediate facility belonging to the X-ray assembly, that itself includes a control facility, and at least one communication interface, and all the control facilities of the X-ray facilities. The control facility of least one of the at least one mobile X-ray facility is configured to control the image recording operation of the respective X-ray facility using control data received from another control facility via the communication connection and/or to transfer at least one recorded image dataset to at least one further control facility via the communication connection.

A method for operating such an X-ray assembly provides that in each case a communication interface of the X-ray facilities establishes a communication connection between the control facilities of the X-ray facilities and/or between an intermediate facility belonging to the X-ray assembly, the intermediate facility itself including a control facility, and at least one communication interface, and all the control facilities of the X-ray facility. The control facility of least one of the at least one mobile X-ray facility controls the image recording operation of the respective X-ray facility using control data received from another control facility via the communication connection and/or transfers at least one recorded image dataset to at least one further control facility via the communication connection.

Embodiments relate to an X-ray assembly in which at least two, for example, exactly two, X-ray facilities are used for a common purpose. The at least one of the X-ray facilities is configured as mobile, e.g. possesses a mobility facility, for example including wheels, that permits automatic and/or manual movement, implemented by a corresponding propulsion appliance, of the mobile X-ray facility in the room in which the X-ray facilities are to be used and beyond. Embodiments include exactly two X-ray facilities in the X-ray assembly, but may include more, for example, in the interaction of three or more X-ray facilities, for a common imaging task, to be greatly simplified.

Embodiments provide communication interfaces the provide the control facilities of the X-ray facilities to communicate directly or indirectly with one another and/or with a, for example central, control facility of an intermediate facility, for example a monitor trolley. This allows the at least one mobile X-ray facility to be "remotely controlled", e.g. to use the transmission of control data via the communication connection to establish a specific image recording operation and/or to collect results of the image recording operation for joint processing with the results from other X-ray facilities at a common location. Finally, the provision of communication interfaces, and hence, therefore, the at least one communication connection, provides for the plurality of X-ray facilities to be understood as a common, at least partially combined, X-ray device, thus simplifying the use of such combined X-ray assemblies in a wide variety of ways. In the simple case of two X-ray facilities, this results, for example, in configurations in which two mobile X-ray facilities or one mobile and one permanently installed X-ray facility communicate directly with one another via the communication connection to coordinate the image recording operation and/or the evaluation/depiction of the image data. In another implementation, the X-ray facilities do not communicate directly, but via at least one further facility, for example, a network, that is logged onto by both X-ray facilities and/or a hospital and/or clinic system. Such networks and/or systems may be an intermediate facility or as including an intermediate facility; however, one implementation variant also provides the use of a, for example, also mobile, local intermediate facility, for example an individual monitor trolley with a depiction facility and an operating facility from which both X-ray facilities may be controlled centrally without the need for further intermediate facilities, e.g. monitor trolleys.

The communication interfaces may be configured for at least partial wireless communication. Wireless communication technologies may be used to establish the communication connection according to the Bluetooth standard and/or the WLAN standard. However, a wired communication connection may be used, e.g., for example, a data communication cable between the respective communication interfaces, that include corresponding connectors. At least partially wired communication may be used. For example, the system may communicate wirelessly, but, at least at times, also use a cable for synchronization tasks.

Furthermore, X-ray facilities may be X-ray facilities with a C-arm at the ends of which the X-ray tube and the X-ray detector of the recording assembly are arranged opposite one another. The at least one mobile X-ray facility that the carrier for the recording assembly includes a C-arm. The mobile X-ray facility may also be referred to as a "mobile C-arm". However, it is also possible for other types of X-ray facilities to be provided as at least one of the X-ray facilities, for example, and this will be dealt with in more detail hereinafter, a sliding gantry CT facility.

In an embodiment, the X-ray facilities may be coupled to one other via the communication connection producing a synchronized multiplane imaging system as an X-ray device providing that the at least two X-ray facilities to be operated centrally via a single operating facility. It is also possible to deactivate operating facilities of other X-ray facilities. The at least one communication connection provides coordinated operation of X-ray facilities in respect of both the image recording operation and the image-processing operation/depiction operation that reduces susceptibility to errors in the X-ray assembly, is conducive to high-quality results, and simplifies the workflow. If a plurality of X-ray facilities include a depiction facility for reproducing recorded image datasets, the communication connections provide for the respective depiction facilities to be used to display image datasets from the other at least one X-ray facility thus, even in the case of strategic placing of the X-ray facilities, for example on both sides of a patient table for mounting the patient, providing image recorded datasets from all the X-ray facilities to be observed thus further enhancing ergonomics.

In an embodiment, due to the mobile X-ray facility's own control facility, the mobile X-ray facility may also be used independently of the remaining at least one X-ray facility, but may be added when required and then removed when not required to save space. An embodiment may include two X-ray facilities that may be used separately on two patient tables/in two rooms but, in rarely occurring cases requiring multilevel imaging, may be coupled to one another in that the X-ray facilities are combined with one another on a patient table and the at least one communication connection is established. This produces an extremely flexible and cost-effective solution.

If a similarly mobile intermediate facility, for example a monitor trolley, is used for a plurality of, e.g. mobile, X-ray facilities, it is possible, instead of only one X-ray facility, to connect two or more X-ray facilities to such an intermediate facility, e.g. a monitor trolley, which still only require one such intermediate facility in the room; moreover, a user may only requires one single operating element, such as, for example, a foot switch. Space-saving results in a more fluid workflow in the examination and/or treatment room and saves time. The omitted intermediate facility, for example, the omitted monitor trolley, reduces the risk of tripping over cables. Since only one single depiction facility is required in the case of one monitor trolley, a user does not have to consider where the X-ray image dataset that has just been recorded is to be displayed, providing more concentrated work. If a wired communication connection is to be used at least two corresponding connectors, for example two connector sockets may be provided on the intermediate facility, e.g. the monitor trolley, as a communication interface.

To improve safety, at least one of the control facilities is configured to authenticate the at least one communication partner during the establishment of communication connection, for example, with the inclusion of a user providing misuse and unauthorized use or the coupling of X-ray facilities that are not intended to be coupled to be avoided. For example, authentication may entail the user inputting a PIN. Additionally, or alternatively, it is also possible for authentication methods that are known to be used.

In an embodiment, a control facility may be configured as the master or specified as the master by the user and/or automatically may be configured for the coordinated control of the entire X-ray assembly. If an in any case central control instance does not automatically present itself, for example in the form of a control facility of an intermediate facility, a control facility may be specified as the master control to implement a central coordinated control of the X-ray system. The other control facilities may be slave control facilities. If one of the X-ray facilities is a permanently installed X-ray facility, the control facility may be automatically used or defined as the master control facility. The master control facility may be hierarchically superior to the slave control facilities and may provide control data for the image recording operation of all the X-ray facilities and/or the image processing for image datasets from all the X-ray facilities. In cases in which no control facility presents itself as the master control facility, for example, if two equally authorized mobile X-ray facilities are provided, the role of the master control facility may be specified by a user and/or automatically, for example in accordance with a random principle. Herein, selection by the user may be preferred since it is then possible for one of the X-ray facilities that is in a better position from the viewpoint of operation to be selected.

If a master control facility is used and if the master control facility is assigned to or belongs to one of the X-ray facilities and this X-ray facility includes an operating facility and a depiction facility, it may expediently be provided that operating facilities and/or depiction facilities of other X-ray facilities are at least temporarily deactivated. In the case of operation by the user, it is also possible to provide that the X-ray facility belonging to or assigned to the master control facility is emphasized thus providing that, as far as possible, confusion during operation or the like may be avoided in advance.

Coordinated control of X-ray facilities may also include the comprehensive, coordinated selection of at least one recording parameter for X-ray facilities that are to be respectively coordinated when in recording operation. For example, the control facility configured as the master may, for example, be configured to select different X-ray spectra for X-ray facilities for which the image datasets are to be jointly evaluated that provides multi-energy imaging, for example, dual-energy imaging. Another example of the assignment of different recording parameters during a common image recording operation is the assignment of different recording geometries to be used for different areas to be covered in the room to X-ray facilities. For example, when two C-arms are used, each of these C-arms may sweep some of the projection angles to be used.

The master control facility is not mandatory for a coordinated operation of if a corresponding negotiating procedure is implemented between control facilities of different X-ray facilities.

In an embodiment, the recording assemblies are assigned adjusting facilities that may be actuated by the respective control facilities for setting different recording geometries. The control facility serving as the master is configured to actuate the adjusting facilities of at least two of the at least two X-ray facilities with kinematic coupling. The adjusting facilities of an X-ray facility, that does not belong to the master control facility, transfer control data via the communication connection to the control facility assigned to the X-ray facility to which the adjusting facilities belong, that converts the control data for the actuation of the adjusting facilities. This provides kinematic coupling of the recording assemblies to one another, that may be employed when using X-ray facilities including C-arms. For example, it may be provided that the control facility serving as the master is configured to maintain at least one constant angle between the alignments of recording assemblies adjusted in a coupled manner.

Coupled operation may require adjusting facilities that provide at least partially automated setting of recording geometries. In an embodiment, it is, for example, possible to use two X-ray facilities each with a C-arm carrying the recording assembly, where the C-arms are arranged rotatably in a common plane, but with a prespecified angular offset to one another, thus providing corresponding images, including with a corresponding difference of the projection angles, to be recorded as specifically different recording geometries. This setting of a relative angle may also take place automatically, for example, when it is possible to retrieve a type of absolute setting with a clear reference and/or some other type of registration exists. It may be possible to exchange at least the current angular positions of the C-arms via the communication connection. If during the kinematic coupling of the X-ray facilities and/or following targeted setting directly after the coupling, the recording assemblies now, for example, have a specific angular difference, for example 90°, the difference is kept constant regardless of the degree to which one of the C-arms is rotated. If, for example, the C-arm of a first one of the X-ray facilities is rotated by 25°, the C-arm of the other X-ray facility is automatically simultaneously also rotated by 25°.

In the case of C-arms that may be rotated about different axes by the adjusting facilities, the angular coupling (or kinematic coupling) may apply to all the possible axes of rotation. For example, an angular coupling to apply to both LAO/RAO rotation and CRA/CAU rotation providing a spherically synchronized movement of C-arms of which at least one belongs to a mobile X-ray facility. Kinematic coupling by keeping difference angles of the different recording assemblies constant with respect to one another is providing in an embodiment. However, in respect of the example of C-arms belonging to two different X-ray facilities and the coupling thereof, it is possible to derive a functionality from two, e.g. independent, X-ray facilities such as that provided with a permanently installed biplane X-ray facility, where, however, a high degree of flexibility is achieved due to the fact that the mobile X-ray facility only needs to be on site when it is actually required.

In an embodiment in which only one of the X-ray facilities includes the necessary adjusting facilities, at least two recording assemblies may be adjusted in a coupled manner, so that one of the recording assemblies is assigned a measuring facility for measuring a manual adjustment of the recording assembly and the remaining recording assemblies are assigned adjusting facilities that may be actuated by the respective control facility for setting different recording geometries. The control facility serving as the master is configured for actuation in a kinematically coupled manner of the adjusting facilities of at least one further one of the at least two X-ray facilities in dependence on a measurement of the measuring facility. If one of the X-ray facilities does not have any automatic possibilities for setting a recording geometry, measuring facilities may be provided that track the current position and the measured values may be used to achieve the kinematic coupling to the other X-ray facilities comprising corresponding adjusting facilities.

With respect of the use of coupled recording geometries, it may be sufficient for corresponding methods to be provided for the acquisition of current settings of the recording assembly at the individual X-ray facilities and a clear reference point defined so that the use of the communication connection results in the provision of relative positional information sufficiently accurate for the X-ray facilities. If, for example, the C-arms are already set manually to a common plane of rotation, simple replacement of current angular positions with respect to a clearly defined reference point may be sufficient to determine the current relative angle between the C-arms. However, for some applications, it may be more expedient for there to be an actual, e.g. complete, registration between coordinate systems of the different X-ray facilities.

For example, it may be provided that at least one control facility, e.g. at least the control facility configured as the master, includes a registration unit for registering coordinate facilities of the different X-ray facilities that provides for the position of components of one X-ray facility also to be made known in control facilities of the other X-ray facilities.

In an embodiment, at least one control facility assigned to at least one X-ray facility includes a collision-avoiding unit for the X-ray facility. The collision-avoiding unit is configured to take account of positional information of at least one further X-ray facility received via the communication connection, e.g. to take account of the at least one mobile X-ray facility in the collision avoidance of the at least one permanently installed X-ray facility. This provides the depth of integration to be increased to form one common X-ray device since a collision avoidance strategy including the entire X-ray assembly may be implemented in the collision-avoiding unit in order to provide the safety of the patient and the avoidance of damage to components to the greatest degree possible. Here, registration is useful in order to identify the positions of the components of other X-ray facilities as accurate as possibly.

The registration unit may be configured to register the coordinate systems using markers provided on the X-ray facilities and/or in the room used by the X-ray facilities. Different specific marker-based approaches may be used for establishing the registration between coordinate systems. Markers may be provided on the floor or the room used on which the at least one mobile X-ray facility may be positioned at the start of the coupling in order to establish a defined initial position to which movements that occur later relate. Floor markings may also be used to reposition the mobile X-ray facility or the like. A detection facility for acquiring the markers may be provided, e.g. an optical and/or electromagnetic detection facility. Floor markings may be identified by electromagnetic and/or optical methods. However, other types of markers, for example recorded features of the patient table may be acquired with, for example, detection facilities provided on the mobile X-ray facility, e.g. on the carrier, thus providing the position of the mobile X-ray facility in the room to be acquired as accurately as possible. Other types of position-determining systems may be used, for example systems using electromagnetic markers.

An embodiment provides that at least one control facility, e.g. the control facility configured as the master is configured to determine instruction data establishing a prespecified relative positioning of at least the recording assemblies of at least two of the at least two X-ray facilities. The instruction data may be output for manual setting via a depiction facility and/or is at least partially used to actuate components serving for positional adjustment of at least one X-ray facility, e.g. after transmission via at least one of the at least one communication connection. When, for example mobility facilities of mobile X-ray facilities also include propulsion appliances, the propulsion appliances may be used automatically to establish suitable relative positions between the X-ray facilities relating to specific desired relative positions between the recording assemblies, that may then, for example, be effected via corresponding, aforementioned adjusting facilities. However, it is also possible to effect suitable relative positionings of the X-ray facilities, e.g. the at least one mobile X-ray facility, in that corresponding instructions are output to a user, who may, for example, refer to the aforementioned flow markings. Thus, it is also possible for a specific positioning to be established manually.

In a development of the present invention, it may be provided that at least one of the control facilities includes a synchronization unit for synchronizing timers of at least two X-ray facilities connected via at least one of the at least one communication connection. The two control facilities to be synchronized may each include a synchronization unit. The synchronization may be used by the control facilities of the X-ray facilities to achieve the same pulse rates and/or the same recording times and/or the like. Different variants may be used for the specific synchronization of X-ray facilities, for example a rapid software synchronization and/or the use of dedicated hardware lines.

An embodiment provides that the X-ray assembly includes at least one permanently installed generator and/or at least one permanently installed cooling facility with connectors for the at least one mobile X-ray facility. To improve the performance of the mobile X-ray facility, in stationary operation, the mobile X-ray facility may be connected to its own, permanently installed generator and/or an additional cooling facility, that is also permanently installed.

At least one of the X-ray facilities, e.g. a permanently installed X-ray facility, may include an imaging system. At least one further one of the X-ray facilities, e.g. a mobile X-ray facility, is configured for the joint use of the imaging system by the transmission of image data via the communication connection. In an embodiment, at least one of the at least one mobile X-ray facility may transmit image data via at least one of the at least one communication connection to a further, permanently installed, X-ray facility with an imaging system and jointly use the imaging system, with respect of common evaluation of the image data. The imaging system may be used for the common evaluation of image data from a plurality of X-ray facilities. For example, the imaging system is also able to reconstruct a three-dimensional image dataset from projection-images image datasets from a plurality of X-ray facilities. The X-ray facility jointly using the imaging system is able to transfer both fully preprocessed image datasets, for example in DICOM format, to the imaging system of the other X-ray facility and raw image data, that is processed in the imaging system in the respective image chain. 3D acquisition operations may be performed individually with X-ray facilities coupled in this way, however it is also possible to perform a synchronized operation with both X-ray facilities, also with different recording parameters in order to cover different X-ray spectra.

The X-ray assembly may include at least one depiction facility for image datasets recorded with the X-ray facilities. For example, the X-ray facilities may also include depiction facilities and/or an intermediate facility, for example a monitor trolley, with a depiction facility. All the other depiction facilities apart from one depiction facility may be deactivated and only to depict the image datasets from all the X-ray facilities on this one depiction facility, and, in many environments and/or for specific examination and/or treatment tasks, to offer the possibility of depicting image datasets from all the X-ray facilities on a plurality of, or even all the, depiction facilities provided. Due to the at least one communication connection, this is possible since the corresponding image datasets between the X-ray facilities or the intermediate facility, therefore the sites of the different depiction facilities, may be exchanged. The depiction facilities may include at least one monitor.

An embodiment provides that the depiction facility is configured for the depiction of two-dimensional projection images recorded under different projection angles, for example, with different X-ray facilities, as image datasets jointly in a 3D visualization in the style of a book. Each page of the book depicted corresponds to a projection image and the pages presented with respect to one another at an angle corresponding to the difference in the projection angles of the respective projection images providing a difference in projection angles between the image planes to be depicted directly in a book-like style since the difference in projection angles is demonstrated by the angular difference of the pages of the book. If more than more two projection images are to be displayed, it is also possible for additional pages to be added to the "book" resulting in an intuitive surgical depiction of two-dimensional image datasets. The user may leaf through the book with ergonomic insight into the differences in the projection angles. The depiction method may also be used independently of the described coupling X-ray facilities via a communication connection.

In an embodiment, a method for depicting two-dimensional images recorded with at least one medical image recording facility on a depiction facility is provided that includes where the images are depicted jointly in a 3D visualization in the style of a book. Each page of the book depicted corresponds to an image and the pages are presented with respect to one another at an angle, corresponding to the angle of the image planes of the respective images. For example, such a visualization method may be used with imaging modalities such as computed tomography and/or magnetic resonance imaging and, in addition to the images, also shows directly in an intuitive manner the angular ratios to one another in that the pages of the book are depicted in the corresponding angular difference to one another. Further two-dimensional images may be easily supplemented by the addition of further pages to the book. Corresponding control elements, that may be provided via a corresponding operating facility or user interface, may provide the book depicted to be leafed through. Thus, multilevel image data is accessible, with the previous depiction of the images page-by-page, the spatial/angular context is concluded from other information, for example from a position of C-arms relative to one another that is visible to the user.

In an embodiment, one of the X-ray facilities is a permanently installed ceiling-suspended X-ray facility with a C-arm, that carries the recording assembly, or a sliding gantry CT facility. Due to the at least one communication connection, the operating and/or depiction facilities are also suitable for use with the at least one mobile X-ray facility. For example, a mobile C-arm may be used as a second plane with a ceiling-suspended angiography system, e.g. a permanently installed X-ray facility with a C-arm, to provide biplane functions. However, there is also the advantage of improved access to the patient or patient table since the mobile X-ray facility may be "parked" a long distance away. A further advantage is that both X-ray facilities may also be used individually, as already demonstrated above.

Dockability with deep integration may be provided, e.g. inclusion of the mobile X-ray facility with respect to the operating facilities, the depiction facilities, the collision avoidance units, the radiation chain and the image chain, to establish the mobile X-ray facility as a component of a clearly defined biplane X-ray device while simultaneously retaining the advantages of both individual X-ray facilities, e.g. with respect to mobility or accuracy. Access to patients is improved and combinations of biplane angiography facilities with sliding gantry CT facilities are also possible without the rotation of the patient if the carrier of the mobile X-ray facility is freely movable and may be removed from the trajectory of the sliding-gantry CT facility.

BRIEF DESCRIPTION OF THE FIGURES

Further advantages and details of the present invention may be derived from the exemplary embodiments described in the following and with reference to the drawings.

FIG. 1 depicts a schematic sketch of a first embodiment of an X-ray assembly according to an embodiment.

FIG. 2 depicts a schematic sketch of a second embodiment of an X-ray assembly according to an embodiment.

FIG. 3 depicts a schematic sketch of a third embodiment of an X-ray assembly according to an embodiment.

FIG. 6 depicts an alternative depiction to that in FIG. 5 in the style of a layer principle.

FIG. 7 depicts a flowchart of a method according to an embodiment.

DETAILED DESCRIPTION

Figure 4:
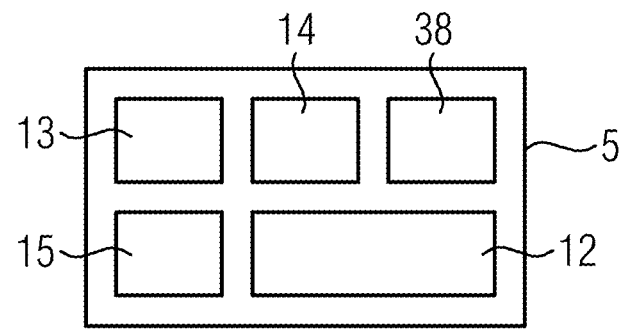
FIG. 4 depicts possible components of control facilities of the X-ray assemblies according to an embodiment.

The embodiments depicted each show two X-ray facilities of an X-ray assembly that may be connected by communications technology; however, the principles depicted here may also be transferred to X-ray assemblies with more than two X-ray facilities.

FIGS. 1 to 3 depict different embodiments. In the X-ray assembly 1a depicted in FIG. 1, two X-ray facilities 2a, 2b may be connected directly without any intermediary via a communication connection 3. To establish the communication connection 3, the X-ray facilities 2a, 2b, of which at least is configured as mobile, include communication interfaces 4 that may be addressed via respective control facilities 5 of the X-ray facilities 2a, 2b. If a wired communication connection 3 is provided, the communication interfaces may include corresponding connectors; however, if it is a purely wireless communication connection 3, for example via Bluetooth and/or WLAN, the communication interfaces 4 are configured as radio interfaces.

FIG. 2 depicts a modified second embodiment of an X-ray assembly 1b that differs from the embodiment in FIG. 1 in that the communication connection 3 is established via a wireless network 6 that is already provided at the location of the X-ray facilities 2a, 2b. The communication connection 3 may be established indirectly via a network component of the network 6. Such a network component may, for example, be a hospital information system (HIS) and/or a radiology information system (RIS).

In the embodiment in FIG. 3, in addition to the X-ray facilities 2a, 2b, the X-ray assembly 1c includes an intermediate facility 7, for example in the form of a monitor trolley, that also has a control facility 5, that may address a communication interface 8 of the intermediate facility 7. The communication interface 8 includes a plurality of, depending upon the embodiment of the communication connections 3, wired and/or wireless connectors 9, thus providing communication connections 3 to be established to all the X-ray facilities 2a, 2b. The intermediate facility 7 also includes a depiction facility 10, e.g. a monitor, and an operating facility 11, that provides both X-ray facilities 2a, 2b to be operated from the intermediate facility 7 and image datasets from both X-ray facilities 2a, 2b to be displayed on the depiction facility 10.

In the embodiments depicted, in each case one of the X-ray facilities 5 provided is used as the master control facility. The other control facilities 5 may be slaves meaning that one of the control facilities 5, e.g. the control facility 5 defined, specified or selected as the master, has a higher hierarchical ranking than the remaining control facilities 5 functioning as slaves. The control facility 5 specified as the master may control the operation of all the X-ray facilities 2a, 2b of the respective X-ray assembly 1a, 1b, 1c in a centrally coordinated manner. The control facility 5 specified as the master may transfer control data to the control facilities 5 specified as slaves, where the slaves may use the control data to control the recording operation of the respective X-ray facility 2a, 2b; simultaneously, the control facility 5 specified as the master is also able to receive image datasets from other X-ray facilities 2a, 2b and use the image datasets for common further processing, for example including depiction. The control facility 5 of the at least one mobile X-ray facility 2a and/or 2b that is used as a slave control facility and thus the corresponding mobile X-ray facility 2a and/or 2b is ultimately coupled in a remotely controllable manner.

In the case of the X-ray assembly 1c, the control facility 5 of the intermediate facility 7 is used as the master control facility; in the case of one of the X-ray facilities 2a, 2b being a permanently installed X-ray facility 2a, 2b, the control facility 5 of this permanently installed X-ray facility 2a or 2b may be used, e.g. defined, as the master control facility. In the case of two mobile X-ray facilities 2a, 2b, if no intermediate facility 7 is provided, the user may select which control facility 5 is the master control facility; an automatic selection, for example a selection based on performed and/or a random selection, is also possible.

FIG. 4 depicts possible subunits that may form part of one or more of the control facilities 5, e.g. the master control facility. FIG. 4 indicates an imaging system 12, that may also be implemented outside the control facility 5. The imaging system 12 implements an image-processing chain, that, with the aid of corresponding hardware and/or software components, provides incoming raw data to be processed to form an X-ray image dataset. Optional, further image-processing steps may be implemented by the imaging system 12. In respect of the transmission of image data from X-ray facilities 2a, 2b, it is possible to receive raw data supplied to the imaging system 12, or, however, at least partially preprocessed image data, that is, for example, already available in the DICOM format. If necessary, if further image-processing steps are to be performed, it is also possible for such image data to be injected into an image-processing chain of the imaging system 12 at a suitable location.

FIG. 4 further depicts an optional authentication unit 13 that provides mutual authentication of communication partners, for example, also with the inclusion of a user, that, for example, inputs a PIN at an operating facility 11 of at least one communication partner in order to release the communication connection and the corresponding coupling.

The registration unit 14 may provide in different ways that there is an at least rough registration of coordinate systems of the individual X-ray facilities 2a, 2b. A rough registration may, for example, be established in that a mobile one of the X-ray facilities 2a, 2b is moved to a specific position, marked by a floor marker, in the room used and positioning is confirmed. Clear reference points may be sufficient for the correlation of angular positions of recording assemblies or general recording geometries. The registration may also be made using optical and/or electromagnetic position-determining systems, that may use passive and/or active markers, that may be, at least partially, also provided on the actual X-ray facilities 2a, 2b. Corresponding detection facilities, that are not depicted, may be used for the markers. For example, at least one mobile one of the X-ray facilities 2a, 2b may include optical and/or electromagnetic sensors that detect markers and hence supply distances from other features, for example, permanently installed features of the room, for example the use of specific features of a patient table, for example on the foot thereof, as markers.

FIG. 4 further depicts a synchronization unit for synchronizing timers of the X-ray facilities 2a, 2b. The synchronization may, for example, be used to achieve the same pulse rates, same recording times and the like. In an embodiment, the master control facility is used since, for example, the master control facility may specify a clock signal. Different synchronization methods may be sued, e.g. the use of software-based synchronization and/or the use of lines specially provided for the synchronization, that may, for example, be connected by the communication interfaces 4.

Figure 5:
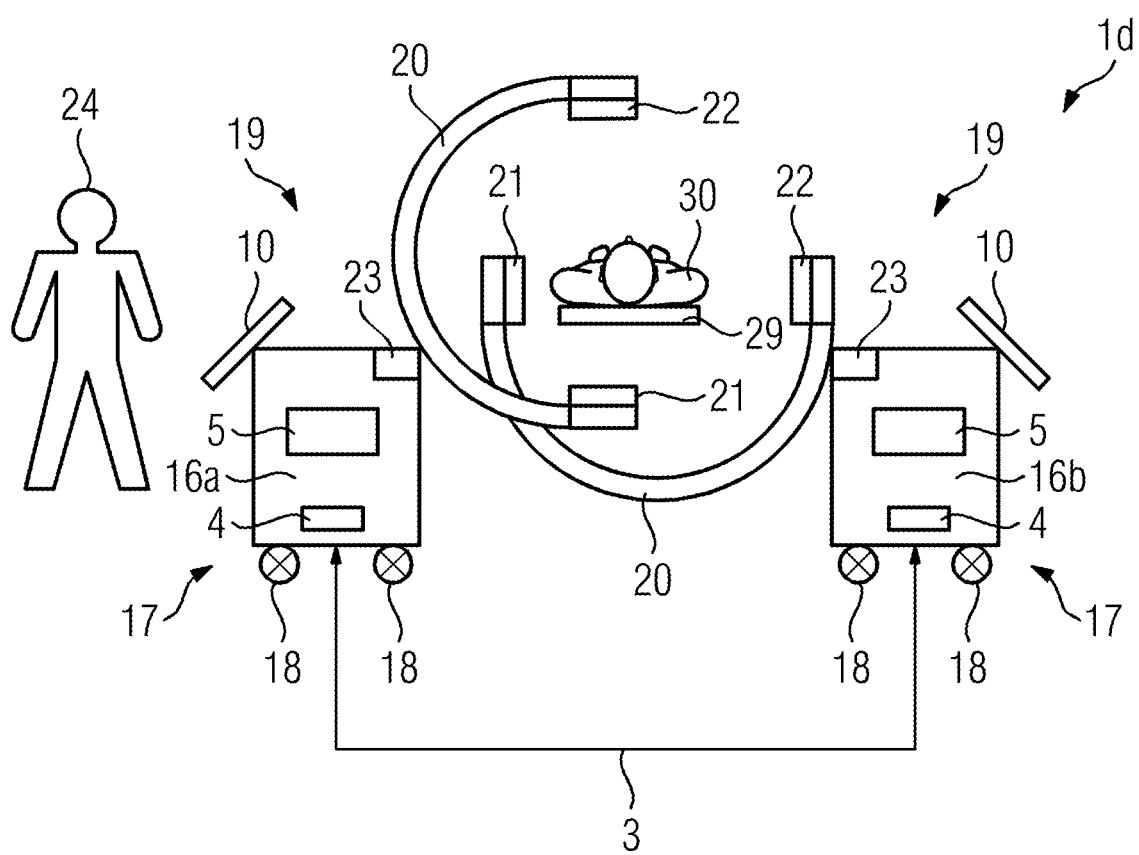
FIG. 5 depicts an embodiment of an X-ray assembly.

FIG. 5 depicts an embodiment of an X-ray assembly 1d. The embodiment includes two mobile X-ray facilities 16a, 16b of which the mobility facility 17 includes wheels 18 and an assigned, optional propulsion appliance, that is not depicted for purposes of clarity. Both the X-ray facilities 16a, 16b include a carrier 19 with in each case a C-arm 20 on which in each case an X-ray tube 21 and an X-ray detector 22 are arranged opposite one another. Therefore, in each case an X-ray tube 21 and an associated X-ray detector 22 form a recording assembly, that is carried by the respective carriers 19. Suitable adjusting facilities 23 permit the automated setting of different recording geometries, for example, also at least one rotation and/or another adjustment of the C-arm 20 and hence the recording assembly. Adjusting facilities 23 may also be assigned to the X-ray tubes 21 and/or the X-ray detectors 22.

The adjusting facilities 23 are actuated by the respective control facilities 5 of the mobile X-ray facilities 16a, 16b. The control facilities 5 may communicate by the communication connection 3 established via the communication interfaces 4, for example, a direct wireless communication connection 3.

Depiction facilities 10 and operating facilities 11, that are not depicted in further detail, are also provided on the carriers 19 of the X-ray facilities 16a, 16b. The master control facility of the control facilities 5 may, for example, be selected by a user 24. Automatic selection methods may be used in the case of the, in principle equally authorized, mobile X-ray facilities 16a and 16b. The user 24 will select the control facility 5 of the X-ray facilities 16a, 16b from which it is easier to take over operation as the master control facility.

FIG. 6 depicts a schematic depiction of the X-ray assembly 1d in a layer structure. A hardware layer 25 is provided by the mobile X-ray facilities 16a, 16b, that may also be called mobile C-arms. The control facilities 5 and the depiction facilities 10 and the operating facilities 11 are depicted in a control layer 26. In a data layer 27, communication data 28, that includes control data, image data and status data, for example the recording geometry currently set, e.g. relating to a projection angle, is transmitted via the communication connection 3.

On the determination of a control facility 5 as the master control facility, the operating facility 11 of the other X-ray facility 16a, 16b may be at least temporarily deactivated, thus providing, therefore, the operation to be performed centrally from one of the X-ray facilities 16a, 16b. The depiction facilities 10, for example including at least one monitor, may, however, be kept active with the two X-ray facilities 16a, 16b, thus providing the user 24 to inspect recorded image datasets from different positions around the patient table 29, that is only indicated here, (see FIG. 5, with patient 30). Since image data may also be transferred via the communication connection 3, image datasets from both X-ray facilities 16a, 16b may be displayed on both depiction facilities 10.

Two mobile X-ray facilities 16a, 16b may interact as a biplane facility, for example, it is possible to achieve a coupled movement of the recording assemblies in the case of simultaneous image acquisition. An example of how this may be done is shown in the method flowchart in FIG. 7. There, at act 31, first the X-ray facilities 16a, 16b are connected for data exchange, i.e., the, for example wireless, communication connection 3 is established. In at act 32, the angular positions of the recording assemblies are set separately for each of the C-arms 20 thus resulting in angular differences, for example in respect of a LAO/RAO axis of rotation and a CRA/CAU axis of rotation. The adaptation of the starting recording geometries may take place manually and/or automatically. Due to the existing communication connection 3, it is possible to actuate both X-ray facilities 16a, 16b, or specifically the adjusting facilities 23 thereof, separately via an operating facility 11 of one of the X-ray facilities 16a, 16b, for example, the one with a control facility 5 that is the master control facility. It is possible, for example, to display a user interface on the respective depiction facility 10 in which the selection of the X-ray facility 16a, 16b to be controlled and specific adjustment commands may be input.

In the case of optionally also automatically moveable X-ray facilities 16a, 16b, i.e. X-ray facilities with a mobility facility 17 including an actuatable controllable propulsion appliance, the basic positioning of the X-ray facilities 16a, 16b may also take place via a central control by the master control facility.

The control facility 5 selected as the master control facility transfers control data via the communication connection 3 to the other control facility 5, where it is correspondingly converted by this control facility 5 selected as a slave control facility in order to actuate the adjusting facilities 23 and optionally the propulsion appliance.

The result of act 32 is the specific setting of relative recording geometries of the recording assemblies of the X-ray facilities 16a, 16b, for example, different angles of rotation of the two axes of rotation and hence angular differences in the two axes of rotation.

In act 33, the user 24 may select, for example in a user interface on the depiction facility 10, a kinematic coupling of the recording assemblies. By this time at the latest, it is expedient to deactivate the operating facility 11 of the slave X-ray facility 16a, 16b. At act 34, the coordinated control of X-ray facilities 16a, 16b for the image recording operation is performed, that is provided both by a specified measuring program and as a result of manual operator inputs by the user 24. At act 34, the angular differences between the recording geometries are always maintained. Each movement of one of the recording assemblies results in automatic actuation of the adjusting facilities 23 for the other recording assembly such that the angular differences as set originally at the time of the kinematic coupling may be maintained. Parallel thereto, in the image recording operation, in a step 35 recorded image datasets from the X-ray facilities 16a, 16b may be depicted on the depiction facilities 10.

At act 36, the kinematic coupling of the X-ray facilities 16a, 16b, is, cleared again, for example, again via an operating element of the user interface. At act 37, it is again possible for independent adjustments or movements of the X-ray facilities 16a, 16b to be performed, thus providing, for example, the relative recording geometries to be reset and the process to be continued with step 32 again.

The procedure described in FIG. 7 using the simple example of at least one maintained relative angle between the recording geometries may also be transferred to other coordinated control approaches, that may be achieved by a central control. For example, in the case of the complete registration of the coordinate systems of the X-ray facilities 16a, 16b, it is possible to plan complete, coordinated movement sequences in advance; it is also possible for other recording parameters to be adapted in a coordinated manner, thus enabling, for example, the two X-ray facilities 16a, 16b to be measured with different X-ray spectra.

In respect of registration, at least one of the control facilities 5 may also include a collision-avoiding unit 38, thus providing, for example in the case of registration by the registration unit 14, positional data received via the communication connection 3 from components of the other X-ray facility 16a, 16b also to be taken into account for overall collision avoidance.

Ultimately deep integration takes place that, if necessary, allows the X-ray facilities 16a and 16b that may also be used individually to be combined as a fully functioning biplane X-ray device, since the slave X-ray facility 16a, 16b is fully included with respect to the operation, collision avoidance and control, for example, both in respect of a radiation chain and in respect of an image chain.

Figure 8:
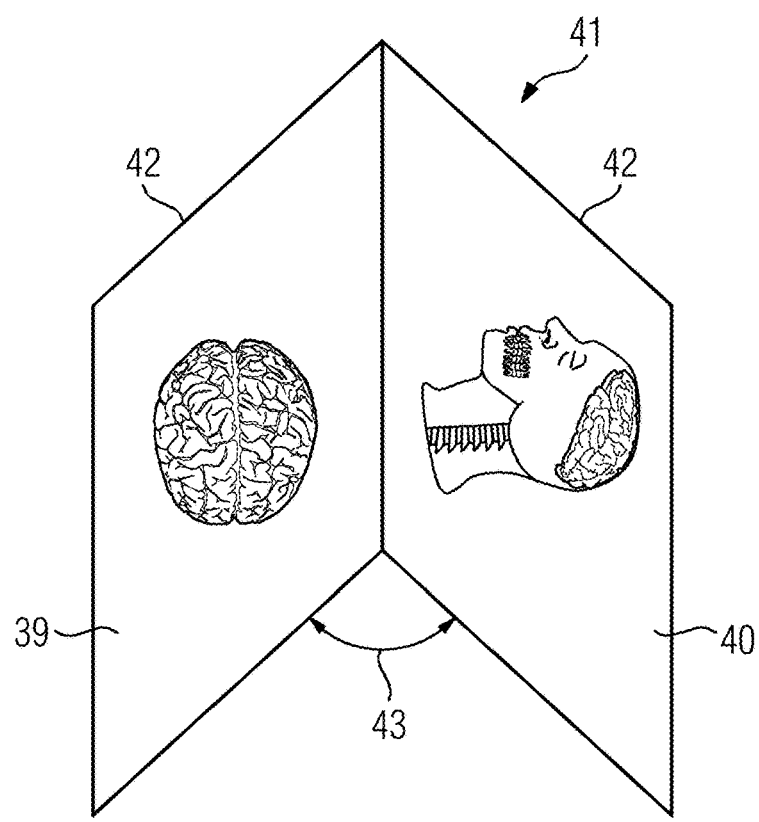
FIG. 8 depicts a possibility for depicting two-dimensional image datasets with different recording geometries according to an embodiment.

FIG. 8 depicts a possibility for the visualization of two-dimensional image datasets, e.g. projection images 39, 40 from the different X-ray facilities 16a, 16b, that were recorded simultaneously. Due to the different angular position of the recording assemblies, different projection angles are provided for the projection images 39, 40. The depiction on the depiction facility 10 is now in the style of a book 41 of which the pages 42 are formed by the projection images 39, 40. The pages 42 are presented in respect to one another such that the aperture angle 43 thereof corresponds to the angular difference between the projection angles of the projection images 39, 40 (and hence the angular difference between the receiving assemblies). The corresponding projection angles may optionally also be inserted in the projection images 39, 40, that are provided with exemplary values (0°, 90°). If further projection images of the visualization are to be added, further pages 42 of the book 41 may be supplemented at the corresponding angular distances; a user 24 is able to "leaf through" the book 41 by suitable operating elements on the operating facility 11 or when the depiction facility 10 is configured as a touchscreen on the depiction facility 10.

This visualization method may also be advantageously used independently of the X-ray assemblies 1a to 1f depicted here, for example with during magnetic resonance imaging.

Figure 9:
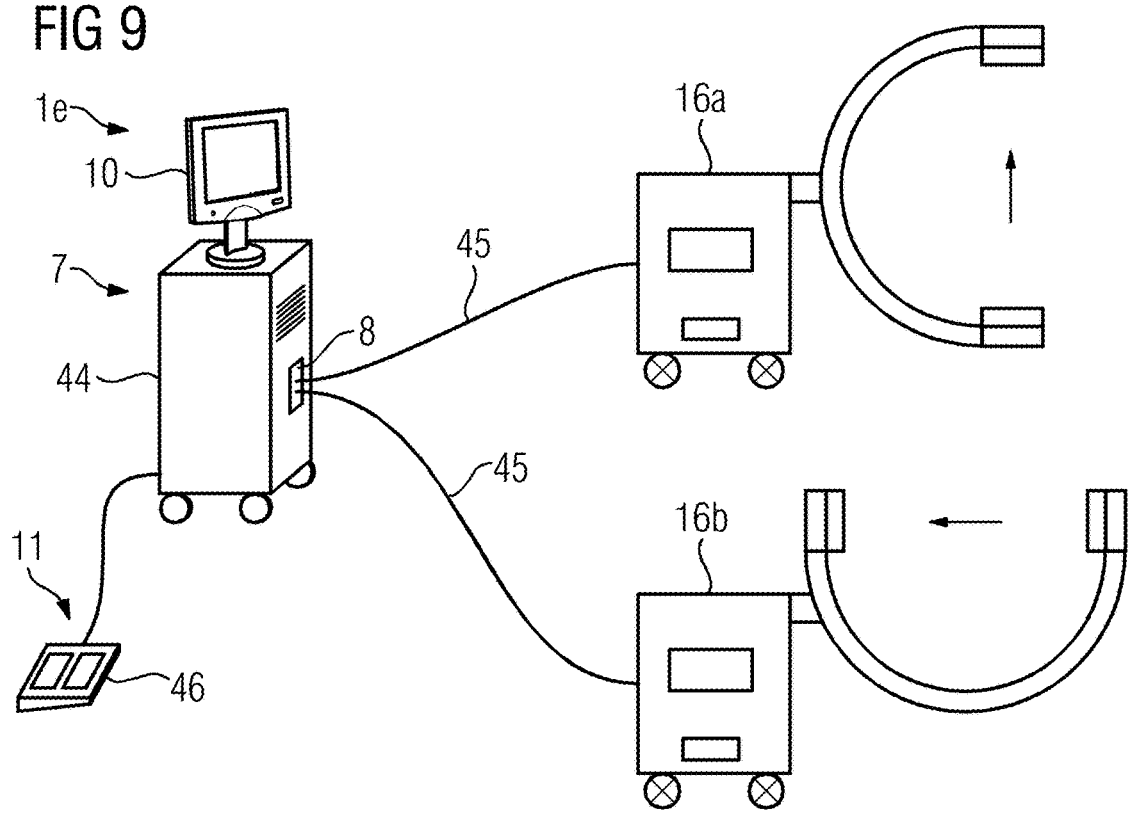
FIG. 9 depicts an embodiment of an X-ray assembly.

FIG. 9 depicts an embodiment an X-ray assembly 1e, that includes an intermediate facility 7 configured as a monitor trolley 44, to which the two mobile X-ray facilities 16a, 16b are connected in the present case via wired cables 45. Accordingly, the communication interface 8 of the intermediate facility 7 includes at least two connectors 9, e.g. connector sockets. A foot switch 46 is depicts as a further frequently used operating facility 11 (or as an operating element), that, since the control facility 5 of the intermediate facility 7 is used as the master control facility, may be used to operate both X-ray facilities 16a, 16b.

Figure 10:
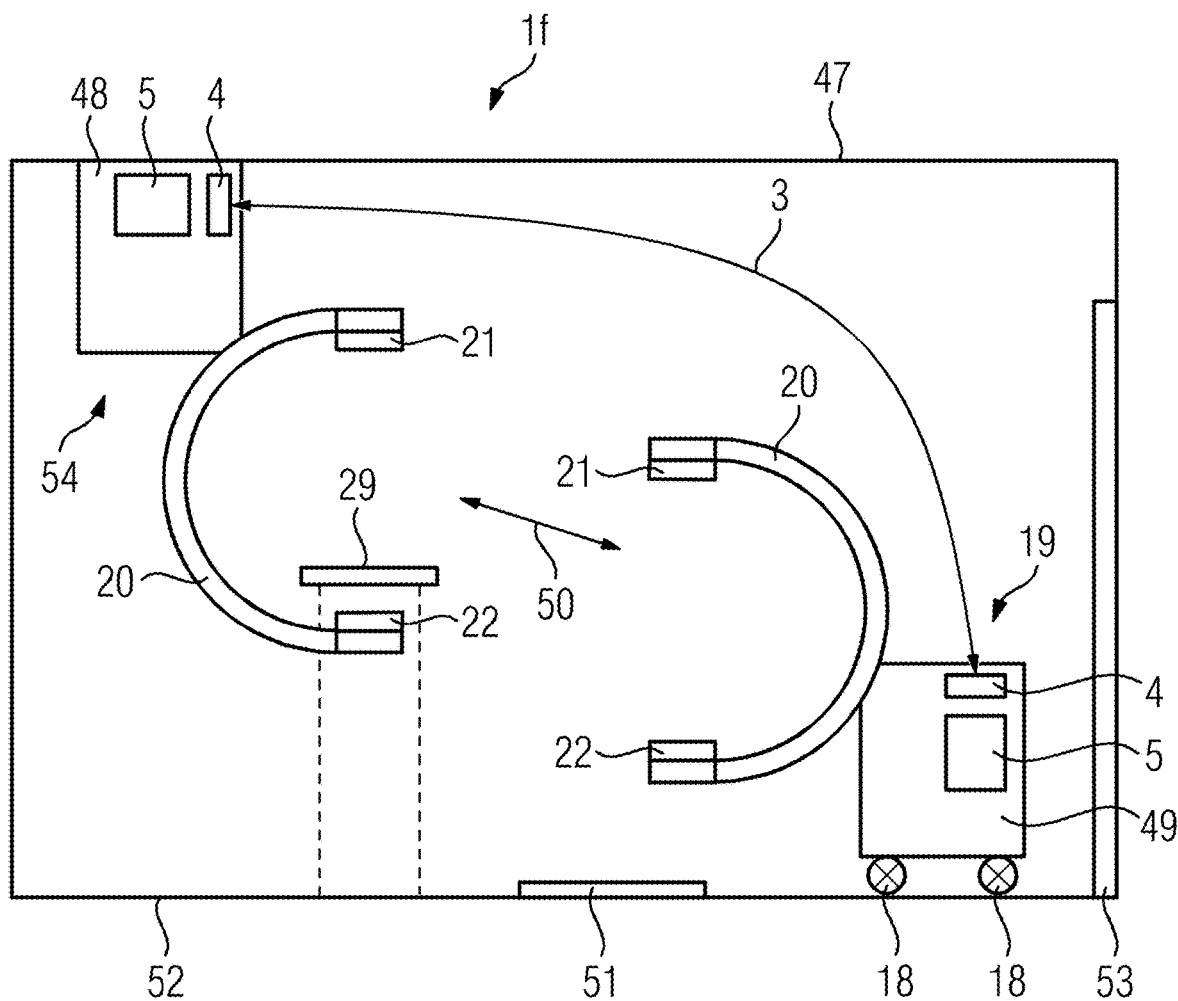
FIG. 10 depicts an embodiment of an X-ray assembly.

FIG. 10 depicts an embodiment of an X-ray assembly 1f in a room 47, in which it is to be used, for example an operating theater as a treatment room. The room 47 also contains a patient table 29.

A first, permanently installed X-ray facility 48 includes a ceiling-mounted carrier 54 with a C-arm 20. A second X-ray facility 49 is configured similarly to the X-ray facilities 16a, 16b. The X-ray facility 49 is mobile and may be moved as desired in relation to the permanently installed X-ray facility 48, as indicated by the arrow 50. The X-ray facility 49 also includes a carrier 19 with a C-arm 20 on which an X-ray tube 21 and an X-ray detector 22 are arranged opposite to another as a recording assembly. Communication interfaces 4 may in turn establish the communication connection 3 directly or indirectly, preferably that depicted in the basic embodiments in FIG. 1 or FIG. 2.

FIG. 10 also depicts a marker 51 on the floor 52 of the room 47, that may, for example, be used for suitable, e.g. initial, positioning of the X-ray facility 49.

The communicative coupling of the X-ray facility 49 to the X-ray facility 48 provides a fully functioning biplane X-ray device to be achieved in which, therefore, two planes are available for recording. Nevertheless, the two X-ray facilities 48, 49 may also be used completely independently of one another if only one plane is required. It is, for example, possible for the X-ray facility 49, that is mobile, to be moved, for example through a door 53 or the like, into a neighboring room, thus providing both X-ray facilities 48, 49 also to be used in parallel independently of one another. This results in a high degree of flexibility. For neurological applications, for example, that require a second plane, the mobile C-arm 20 of the X-ray facility 49 may be coupled-on.

In addition to the ceiling-mounted X-ray facility 48 and/or alternatively thereto, in FIG. 10 it is also possible to use a sliding-gantry CT facility thus also providing three X-ray facilities on one X-ray assembly.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. An X-ray assembly comprising:
at least two X-ray facilities, each X-ray facility of the at least two X-ray facilities comprising:
a control facility;
a recording assembly comprising an X-ray tube and an X-ray detector, wherein at least one X-ray facility of the at least two X-ray facilities is a mobile X-ray facility with a mobile carrier carrying the recording assembly; and
a communication interface configured to establish a communication connection between control facilities of the at least two X-ray facilities, respectively, between an intermediate facility belonging to the X-ray assembly, which comprises a control facility and at least one communication interface, and all control facilities of the at least two X-ray facilities, or between the control facilities of the at least two X-ray facilities, respectively, and between the intermediate facility and all the control facilities of the at least two X-ray facilities, wherein the respective control facility of one or more mobile X-ray facilities of the at least one mobile X-ray facility is configured to control an image recording operation of the respective X-ray facility using control data received from another control facility of the at least two X-ray facilities and the intermediate facility via the respective communication connection, transfer at least one recorded image dataset to at least one further control facility of the at least two X-ray facilities and the intermediate facility via the respective communication connection, or a combination thereof.

2. The X-ray assembly of claim 1, wherein the communication interfaces are configured for wireless communication, the mobile carrier includes a C-arm, or the communication interfaces are configured for wireless communication and the mobile carrier includes the C-arm.

3. The X-ray assembly of claim 1, wherein a control facility of the at least two X-ray facilities is configured as a master control facility, is specified as the master control facility by a user, is automatically configured for coordinated control of the X-ray assembly, or any combination thereof.

4. The X-ray assembly of claim 3, wherein the recording assemblies are assigned adjusting facilities that are actuatable by respective control facilities for setting different recording geometries, and
wherein the control facility serving as the master control facility is configured to actuate the adjusting facilities of two or more X-ray facilities of the at least two X-ray facilities with kinematic coupling.

5. The X-ray assembly of claim 1, wherein at least one control facility of the at least two X-ray facilities and the intermediate facility comprises a registration unit configured to register coordinate facilities of the at least two X-ray facilities.

6. The X-ray assembly of claim 5, wherein a control facility of the at least two X-ray facilities is configured as a master control facility, is specified as the master control facility by a user, is automatically configured for coordinated control of the X-ray assembly, or any combination thereof, and
wherein the at least one control facility comprises the master control facility.

7. The X-ray assembly of claim 5, wherein one or more control facilities assigned to one or more X-ray facilities of the at least two X-ray facilities, respectively, comprise a collision-avoiding unit for the respective X-ray facility, and
wherein the respective collision-avoiding unit is configured to take account of positional information of at least one further X-ray facility of the at least two X-ray facilities received via a respective communication connection.

8. The X-ray assembly of claim 5, wherein one or more control facilities of the at least two X-ray facilities are configured to determine instruction data establishing a pre-specified relative positioning of at least the recording assemblies of two or more X-ray facilities of the at least two X-ray facilities, are at least partially used to actuate components serving for positional adjustment of at least one X-ray facility of the at least two X-ray facilities, or are configured to determine the instruction data and are at least partially used to actuate the components.

9. The X-ray assembly of claim 8, wherein the one or more control facilities are at least partially used to actuate the components after transmission via at least one of the communication connections.

10. The X-ray assembly of claim 1, wherein at least one control facility of the at least two X-ray facilities comprises a synchronization unit configured for synchronizing timers of two or more X-ray facilities of the at least two X-ray facilities connected via at least one of the communication connections.

11. The X-ray assembly of claim 1, further comprising:
at least one permanently installed generator;
at least one permanently installed cooling facility with connectors for the at least one mobile X-ray facility; or
a combination thereof.

12. The X-ray assembly of claim 1, wherein one or more X-ray facilities of the at least two X-ray facilities comprise an imaging system, and
wherein at least one further X-ray facility of the at least two X-ray facilities is configured for a common use of the imaging system.

13. The X-ray assembly of claim 12, wherein the one or more X-ray facilities comprise a permanently installed X-ray facility, and
wherein the at least one further X-ray facility comprises a mobile X-ray facility.

14. The X-ray assembly of claim 12, wherein the imaging system is configured for a common evaluation of image data from the at least two X-ray facilities.

15. The X-ray assembly of claim 1, further comprising:
at least one depiction facility for image datasets recorded with the at least two X-ray facilities.

16. The X-ray assembly of claim 15, wherein the depiction facility is configured for a depiction of two-dimensional (2D) projection images recorded under different projection angles as image datasets jointly in a three-dimensional (3D) visualization in the style of a book, and
wherein each page of the book depicted corresponds to a projection image, and the pages are presented with respect to one another at an angle corresponding to a difference in the projection angles of the respective projection images.

17. The X-ray assembly of claim 1, wherein one X-ray facility of the at least two X-ray facilities is a permanently installed ceiling-suspended X-ray facility with a C-arm that carries the recording assembly, or a sliding-gantry CT facility, and
wherein, due to the at least one communication connection, operating facilities, depiction facilities, or operating and depiction facilities are also configured for use with the at least one mobile X-ray facility.

18. A method for operating an X-ray assembly including at least two X-ray facilities each comprising a control facility and a recording assembly, the respective recording assembly comprising an X-ray tube and an X-ray detector, at least one X-ray facility of the at least two X-ray facilities being a mobile X-ray facility with a mobile carrier carrying a recording assembly carrier, the method comprising:
establishing, by a communication interface of the at least two X-ray facilities, a communication connection between control facilities of the at least two X-ray facilities, between an intermediate facility belonging to the X-ray assembly and all control facilities of the at least two X-ray facilities, or between the control facilities of the at least two X-ray facilities and between the intermediate facility and all the control facilities of the at least two X-ray facilities, the intermediate facility comprising a control facility and at least one communication interface; and
controlling, by the control facility of one or more mobile X-ray facilities of the at least one mobile X-ray facility, an image recording operation of the respective X-ray facility using control data received from another control facility of the at least two X-ray facilities via the communication connection, transferring at least one recorded image dataset to at least one further control facility of the at least two X-ray facilities via the communication connection, or a combination thereof.

* * * * *